US007691836B2

(12) United States Patent
Hamersma et al.

(10) Patent No.: US 7,691,836 B2
(45) Date of Patent: Apr. 6, 2010

(54) PROGESTERONE RECEPTOR MODULATORS

(75) Inventors: Johannes Antonius Maria Hamersma, Oss (NL); Johannes Bernardus Maria Rewinkel, Oss (NL)

(73) Assignee: N.V. Organon, Oss (NL)

( * ) Notice: Subject to any disclaimer, the term of this patent is extended or adjusted under 35 U.S.C. 154(b) by 532 days.

(21) Appl. No.: 10/594,103

(22) PCT Filed: Mar. 18, 2005

(86) PCT No.: PCT/EP2005/051265

§ 371 (c)(1),
(2), (4) Date: Sep. 25, 2006

(87) PCT Pub. No.: WO2005/092912

PCT Pub. Date: Oct. 6, 2005

(65) Prior Publication Data
US 2007/0203105 A1 Aug. 30, 2007

Related U.S. Application Data

(60) Provisional application No. 60/556,210, filed on Mar. 25, 2004.

(30) Foreign Application Priority Data
Mar. 25, 2004 (EP) .................................. 04101241

(51) Int. Cl.
A61K 31/58 (2006.01)
C07J 3/00 (2006.01)
C07J 43/00 (2006.01)
C07J 53/00 (2006.01)

(52) U.S. Cl. .................. 514/176; 540/47; 540/107; 552/611

(58) Field of Classification Search .............. 514/176; 540/47, 107; 552/611
See application file for complete search history.

(56) References Cited

U.S. PATENT DOCUMENTS

| 5,084,450 A | 1/1992 | Gaillard-Kelly et al. | 514/177 |
| 5,273,971 A | 12/1993 | Scholz et al. | 514/176 |
| 5,688,810 A | 11/1997 | Jones et al. | 514/311 |

FOREIGN PATENT DOCUMENTS

| DE | 36 17 883 A1 | 12/1986 |
| DE | 290 198 | 5/1991 |
| EP | 0 303 306 B1 | 2/1989 |
| EP | 0 349 481 B1 | 1/1990 |
| EP | 0 549 041 B1 | 6/1993 |
| EP | 0 582 338 B1 | 2/1994 |
| EP | 0 277 676 B1 | 8/1998 |
| EP | 0 289 073 B1 | 11/1998 |
| EP | 0 876 815 B1 | 11/1998 |
| GB | 2 175 905 A | 12/1986 |
| WO | WO 97/49407 A1 | 12/1997 |
| WO | WO 99/25360 A2 | 5/1999 |
| WO | WO 99/25360 A3 | 5/1999 |
| WO | WO 99/45022 A1 | 9/1999 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26) state "Predicting the formation of solvates or hydrates of a compound and the number of molecules of water or solvent incorporated in to the crystal lattice of a compound is complex and difficult."*
International Search Report Application No. PCT/EP2005/051265 dated Jul. 21, 2005.
Written Opinion of International Application No. PCT/EP2005/051265.
Derwent Abstract No. 0005691763 abstracting DD 290 198.
Cook, C. E. et al., "Reversal of Activity Profile in Analogs of the Antiprogestin Ru 487: Effect of a 16α-Substituent on Progestational (Agonist) Activity," Life Sciences, vol. 52 (1993) pp. 155-162.
Van den Heuvel, J. J. et al., "Synthesis of 6β-methyl analogues of mifepristone, new selective antiprogestagens," Recl. Trav. Chim. Pays-Bas, vol. 112 (1993) pp. 107-112.
Mash, E. A. et al., "Mechanistic Studies of Diastereoselective Cyclopropanation via Homochiral Ketals. 1. Dioxolane Structural Effects," J. Org. Chem., vol. 55 (1990) pp. 2045-2055.
Beato, M. et al., "General Review—DNA Regulatory Elements for Steroid Hormones," J. steroid Biochem , vol. 32, No. 5 (1989) pp. 737-747.
Sauer, J. et al., "1,2,4,5-Tetrazine: Synthesis and Reactivity in [4+2] Cycloadditions," Eur. J. Org. Chem. (1998) pp. 2885-2896.
Heldmann, D. K. et al., "Synthesis of Metallated (Metal = Si, Ge, Sn) Pyridazines by Cycloaddition of Metal Substituted Alkynes to 1,2,4,5-Tetrazine," Tetrahedron Letters, vol. 38, No. 33 (1997) pp. 5791-5794.
Schoonen, W.G.E.J. et al., Notes & Tips, Analytical Biochemistry, vol. 261 (1998) pp. 222-224.

* cited by examiner

Primary Examiner—Barbara P Badio
(74) Attorney, Agent, or Firm—Susan Hess

(57) ABSTRACT

The subject invention provides a compound according to Formula I, wherein

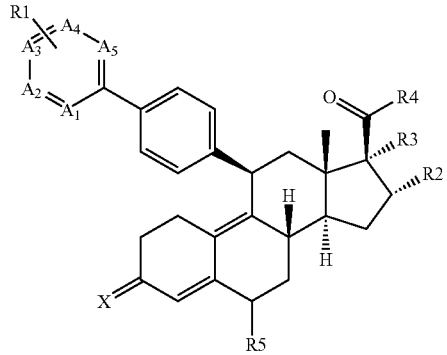

each of the substituents is given the definition as set forth in the specification and claims, or a pharmaceutically acceptable salt and/or hydrate form and/or prodrug thereof.

28 Claims, No Drawings

PROGESTERONE RECEPTOR MODULATORS

FIELD OF THE INVENTION

The present invention relates to the field of contraception, hormone replacement therapy (HRT) and therapy of gynaecological disorders, as well as adjuvant therapy in cancer and other diseases.

The subject invention provides novel progesterone receptor modulating steroids which have both agonistic and antagonistic modulating activities towards the progesterone receptor, processes for their preparation, and their use in therapy.

BACKGROUND OF THE INVENTION

Intracellular receptors are a class of structurally related proteins involved in the regulation of gene transcription. Steroid receptors are a subset of these receptors, including the progesterone receptor (PR), androgen receptor (AR), estrogen receptor (ER), glucocorticoid receptor (GR) and mineralocorticoid receptor (MR). Regulation of a gene requires the intracellular receptor and a corresponding ligand which has the ability to selectively bind to the receptor in a way that affects gene transcription.

Progesterone receptor modulators (progestagens and antiprogestagens) are known to play an important role in the health of women. The natural ligand for PR is the steroid hormone progesterone, but synthetic compounds have been made which may also serve as ligands (see e.g. Jones et al U.S. Pat. No. 5,688,810).

Progestagens are currently widely used for hormonal contraception and in HRT. Other important clinical applications of progestagens are treatment of gynaecological disorders (e.g. endometriosis, dysmenorrhea, dysfunctional uterine bleeding, severe premenstrual syndrome), breast cancer, hot flushes and mood disorders, and luteal support during IVF. In addition, they are applied in combination with other hormones and/or other therapies including, without limitation, chemotherapeutic agents such as cytotoxic and cytostatic agents, immunological modifiers such as interferons and interleukins, growth hormones or other cytokines, hormone therapies, surgery and radiation therapy.

The current steroidal progestagens have been proven to be quite safe and are well tolerated. Sometimes, however, side effects (e.g. breast tenderness, headaches, depression, and weight gain) have been reported that are attributed to these steroidal progestagens, either alone or in combination with estrogenic compounds. In addition, steroidal ligands for one receptor often show cross-reactivity with other steroidal receptors. Many progestagens also bind e.g. to the androgen receptor, whereas many antiprogestagens have affinity for the glucocorticoid receptor.

Antiprogestagens in combination with progestagens are also useful in contraceptive and hormone replacement regimens as described e.g. in WO 99/25360 and WO 97/49407. It would therefore be useful to find compounds which have both progestagenic and antiprogestagenic properties within one molecule.

WO 99/45022 describes 20-keto-11β-arylsteroids which have either antagonistic or agonistic activity towards the progesterone receptor. Of the many compounds disclosed in WO 99/45022, three or four compounds have both progesterone antagonist and agonist activity. None of these compounds has a substituent in position 16; in position 17α, they have an acetyloxy, acetyloxymethyl or methoxymethyl substituent.

The compounds described in EP 349481 contain a 4-[(3-pyridyl)phenyl] substituent in position 11β and have no substituent in position 16; none of these compounds possesses a cyclopropylcarbonyl or cyclopropenylcarbonyl substituent in position 17, nor a spirocycloalkanone or spirocycloalkenone substituent in position 17. The compounds of EP 349481 have antiprogestagenic properties only.

The subject invention now surprisingly discloses that novel steroid compounds with an (11β)-[4-(aza-aryl)phenyl] substituent in combination with a variety of substituents in positions 16 and 17 show a mixed profile of PR agonist and PR antagonist activity (hereinafter referred to as mixed P/AP profile) within one compound. These compounds are particularly useful for contraction, HRT and the treatment of gynaecological disorders. Cook et al. (Life Sciences 52 (1993), 155-162) describes the possibility that a steroid which has an antiprogestagenic profile with an acetyloxy substituent at the 17α position can be turned into a compound with a mixed profile by deleting this substituent, while introduction of a substituent in the 16α position turns the compound into a full agonist Surprisingly, this is not the case for the novel compounds disclosed in the subject invention, which uniformly have mixed profiles with various combinations (including hydrogen) of 16α- and 17α-substituents.

DETAILED DESCRIPTION OF THE INVENTION

The subject invention provides a compound of structural Formula I

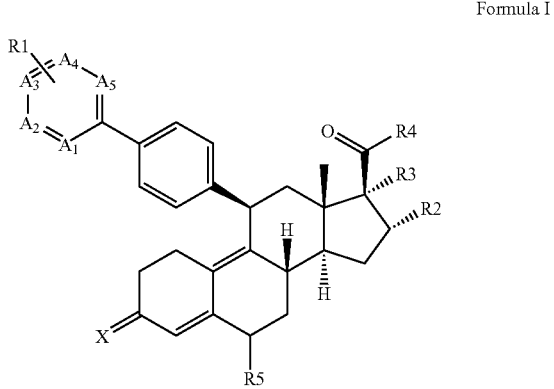

Formula I wherein

X is O, NOH, NO(1-4C)alkyl, NO(1-4C)acyl;

A1-A5 are C, substituted with R1, or N, provided that at least one and not more than three of A1-A5 are N; or one or two of A1, A2 and A5 are N, and the others are C, substituted with R1, and A3 and A4 together represent a fused benzo ring or a fused five- or six-membered nitrogen-containing aromatic ring, both optionally substituted with one or more halogen and/or (1-4C)alkyl;

each R1 is independently selected from H, halogen, (1-4C)alkyl and (1-4C)alkoxy;

R2 is H, (1-4C) alkyl or (1-6C) alkenyl, both optionally substituted with an (6-10C)aryl group, which is optionally substituted with one or more halogen and/or (1-4C)alkyl; and R3 is H or (1-4C)alkyl, optionally substituted with one or more halogen atoms; and
R4 is cyclopropyl or cyclopropenyl, both optionally substituted with one or more halogen and/or (1-4C)alkyl; or
R2 together with R3 forms a 3-, 4-, 5- or 6-membered carbocyclic ring; and
R4 is cyclopropyl or cyclopropenyl, both optionally substituted with one or more halogen and/or (1-4C)alkyl; or
R2 is H or (1-4C)alkyl; and
R3 together with R4 forms a 5-, 6- or 7-membered saturated or unsaturated carbocyclic ring
R5 is H or (1-4C)alkyl;

or a pharmaceutically acceptable salt and/or hydrate form and/or prodrug thereof.

In one embodiment, A1-A5 are C, substituted with R1, or N, provided that at least one and not more than three of A1-A5 are N.

In another embodiment, one or two of A1, A2 and A5 are N, and the others are C, substituted with R1, and A3 and A4 together represent a fused benzo ring or a fused nitrogen-containing ring, both optionally substituted with halogen and/or (1-4C)alkyl.

In one embodiment, R2 is H, (1-4C)alkyl or (1-6C)alkenyl, both optionally substituted with an (6-10C)aryl group, which is optionally substituted with one or more halogen and/or (1-4C)alkyl; and R3 is H or (1-4C)alkyl, optionally substituted with one or more halogen; and R4 is cyclopropyl or cyclopropenyl, both optionally substituted with one or more halogen and/or (1-4C)alkyl.

In another embodiment, R2 together with R3 forms a 3-, 4-, 5- or 6-membered carbocyclic ring; and R4 is cyclopropyl or cyclopropenyl, both optionally substituted with one or more halogen and/or (1-4C)alkyl.

In yet another embodiment, R2 is H or (1-4C)alkyl; and R3 together with R4 forms a 5-, 6- or 7-membered saturated or unsaturated carbocyclic ring.

In a specific embodiment, X is O.

In another specific embodiment, R4 is cyclopropyl.

In yet another specific embodiment, A1, A3, A4 and A5 are C, substituted with R1, and A2 is N.

In one embodiment R2 is H, (1-4C)alkyl or (1-4C)alkenyl.

In a specific embodiment, X is O, A1, A3, A4 and A5 are C, substituted with R1, and A2 is N; R2 is H, (1-4C)alkyl or (1-4C)alkenyl; and R3 is H or (1-4C)alkyl, optionally substituted with one or more halogen; and R4 is cyclopropyl; or
R2 together with R3 forms a 3-, 4-, 5- or 6-membered carbocyclic ring; and
R4 is cyclopropyl.

In a particular embodiment, X is O, A1, A3, A4 and A5 are C; A2 is N; R1 is H; R2 is methyl; R3 is H; R4 is cyclopropyl; and R5 is H In another particular embodiment, X is O, A1, A3, A4 and A5 are C; A2 is N; R1 is H; R2 is ethenyl; R3 is H; R4 is cyclopropyl; and R5 is H.

The compounds of the subject invention are envisaged for use in therapy.

The subject invention provides a pharmaceutical composition comprising a compound of the subject invention and a pharmaceutically acceptable carrier. In one embodiment, a pharmaceutical composition is envisaged for contraception. In another embodiment, a pharmaceutical composition is envisaged for hormone replacement therapy. In yet another embodiment, a pharmaceutical composition is envisaged for the treatment of a gynaecological disorder.

The subject invention further involves a use of a compound of the subject invention for the manufacture of a medicament In one embodiment, a use of a compound of the subject invention is for the manufacture of a contraceptive. In another embodiment, a use of a compound of the subject invention is for the manufacture of a medicament for hormone replacement therapy or for the treatment of a gynaecological disorder.

The subject invention further provides a method of contraception comprising administering a pharmaceutically effective amount of a compound of the subject invention to a subject in need thereof.

The subject invention further provides a method of treating a gynaecological disorder comprising administering a pharmaceutically effective amount of a compound of the subject invention to a subject in need thereof.

Compounds of Formula I wherein X is NOH, NO(alkyl) or NO(acyl) were prepared from compounds of Formula I wherein X is O by treatment with $H_2NOH$, $H_2NO(alkyl)$ or $H_2NO(acyl)$ or salts of these amines.

As depicted in Scheme 1 compounds of Formula I wherein X is O (Formula I in Scheme 1) were prepared from compounds of Formula II. In this scheme Pg was a suitable protecting group of the carbonyl function at position 3 of the steroids. Several protecting groups known in the art are described in "Protective Groups In Organic Synthesis" by Greene T. W. and Wuts P. G. M. (John Wiley & Sons, New York). Suitable types of protective groups are ketals; in particular, cyclic ketals such as 1,3-dioxolanes are suited. The carbonyl group at position 17 of the steroid was used as such in this reaction sequence, or was masked in the form of a synthetic equivalent such as an hydroxymethyl group (which at a later moment in the synthesis was oxidized back to a carbonyl). Another option is protection of the carbonyl by a protecting group such as ketal.

Compounds of Formula II were oxidized to an epoxide of Formula III using various methods known in the art such as treatment with hydrogen peroxide in the presence of trifluoroacetophenone. Treatment of such an epoxide with (4-bromophenyl)magnesium bromide in the presence of a suitable Cu(I) salt such as copper(II) chloride yielded compounds of Formula IV. Compounds of Formula IV were transferred into compounds of Formula V using palladium-mediated cross-coupling reactions such as the Suzuki, Stille or Negishi reactions. Removal of the protecting group of compounds of Formula V using methods known in the art such as, in the case of ketals, aqueous acid afforded compounds of Formula I. Such methods of deprotection can be applied to compounds of Formula IV to give compounds of Formula VI. The latter compounds can be transferred into compounds of Formula I using palladium-mediated cross-coupling reactions.

Compounds of Formula II in which R4 is cyclopropyl or cyclopropenyl were prepared from compounds of Formula VII as depicted in Scheme 2. Compounds of Formula VII are described in the literature (e.g. van den Heuvel, M. J. and Groen, M. B. Rec. Trav. Chim. Pays-Bas, 112, 107 (1993), EP289073, EP277676, DE3617883, EP549041, EP 582338). Compounds of Formula VII were transformed into enol triflates using a base and triflating reagent. An example of a suitable combination of reagents is lithium hexamethyldisilazane as base followed by addition of N-phenyl-bis(trifluoromethanesulfonimide) as triflating agent The resulting enol triflates were transferred into compounds of Formula VIII using a palladium-mediated carbonylation in the presence of N,O-dimethylhydroxylamine. Treatment of compounds of Formula VIII with cyclopropyl-Grignard, cyclopropyllithiate, cyclopropenyl-Grignard, or cyclopropenyllithiate yields compounds of Formula IX. Treatment of the latter compounds with an R2-lithiate or R2-Grignard compound in the presence of a suitable Cu(I) salt followed by quenching with water yields compounds of Formula II wherein R3 is H; alternatively, quenching with an alkylating reagent such as methyl iodide or the like yields compounds of Formula II wherein R3 is alkyl.

Compounds of Formula II where R3 together with R4 forms a 5-membered carbocyclic ring can be prepared using the method described in U.S. Pat. No. 5,084,450. In general, compounds of Formula II where R3 together with R4 forms a 5-, 6- or 7-membered carbocyclic ring can be prepared from compounds of Formula VII using the method described by Mash, E. A. et al. in J. Org. Chem. 55, 2045 (1990). In this publication the method was applied to transform a ketone into a 6-membered spiro compound. This method can be extended to 5- or 7-membered spiro compounds by using 4-iodobutyl tert-butyldimethylsilyl ether or 6-iodohexyl tert-butyldimethylsilyl ether instead of the 5-iodopentyl tert-butyldimethylsilyl ether applied in the publication to prepare a 6-membered spiro compound.

Scheme 1

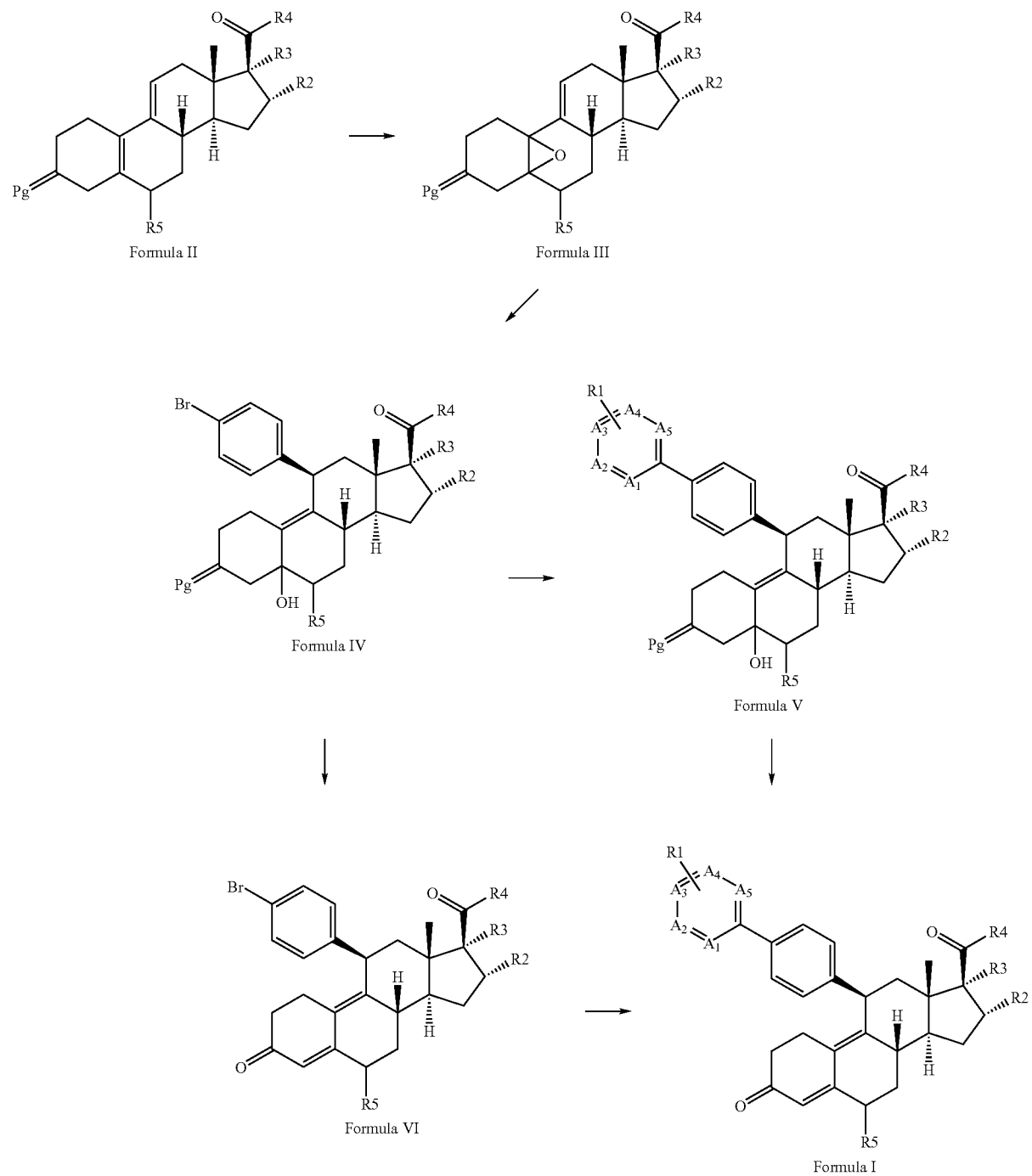

Scheme 2

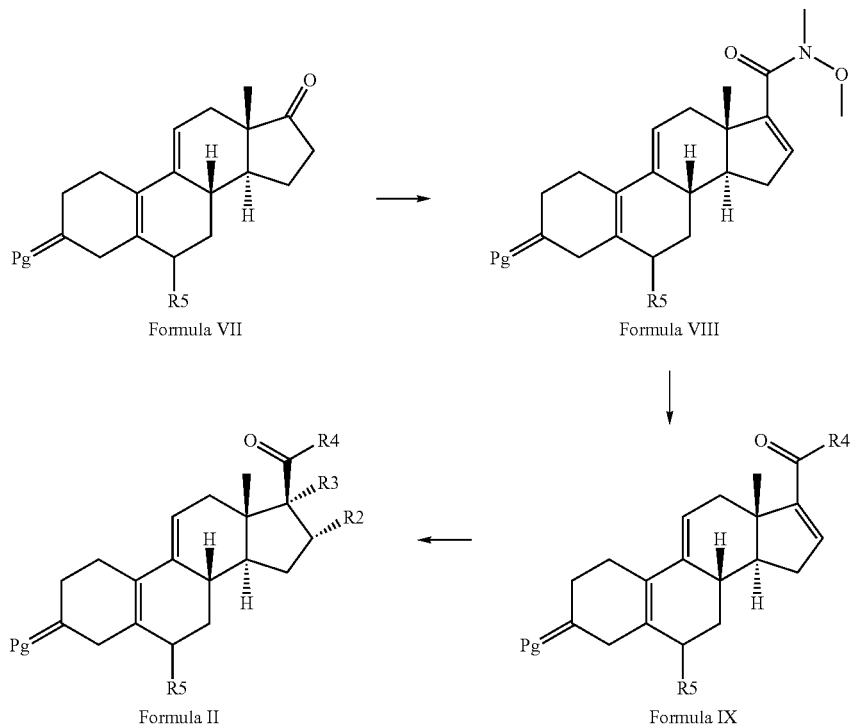

A compound according to the invention is a compound as defined above in Formula I, a salt thereof, a hydrate thereof and/or a prodrug thereof.

In those cases that a compound of the invention contains a nitrogen atom of suitable basicity, the compound may be used as a free base or as a pharmaceutically acceptable salt.

The term pharmaceutically acceptable salt represents those salts which are, within the scope of medical judgement, suitable for use in contact with the tissues of humans and/or animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like.

Prodrugs represent compounds which are rapidly transformed in vivo to the parent compound of the above formula, for example by hydrolysis in the stomach and/or in the blood, metabolism in the liver or other processes known to those skilled in the art. For instance, those skilled in the art will recognize that compounds of Formula I where X is $H_2$ can be expected to be metabolized to the analogous compounds where X is O, which show activity in vitro even if the prodrug where X is $H_2$ does not.

The terms used in the definition of the compounds of the invention according to formula I have the following meaning:

(1-4C)alkyl is a branched or unbranched alkyl group having 1-4 carbon atoms, for example methyl ethyl, propyl, isopropyl butyl, sec-butyl or tert-butyl;

(1-4C)alkoxy means (1-4C)alkyloxy, wherein (1-4C)alkyl has the meaning as defined above;

(1-6C)alkenyl is a branched or unbranched alkenyl group having 1-6 carbon atoms, such as ethenyl, 1-methyl-ethenyl, 2-propenyl 2-butenyl and the like;

(6-10)aryl is a carbocyclic aromatic group having 6-10 carbon atoms, such as phenyl 1-naphthyl or 2-naphthyl;

(1-4C)acyl is an alkylcarbonyl group having 1-4 carbon atoms, such as formyl, acetyl or propionyl;

aza-aryl means a monocyclic or bicyclic aromatic ring system, in which at least one of the rings contains at least one nitrogen ring atom. Examples include, but are not limited to, pyridyl pyrimidinyl quinolinyl naphthyridyl and the like;

carbocyclic, when mentioned in the context of a ring, means that all the atoms constituting the ring are carbon atoms;

spirocycloalkane is a substituent consisting of an alkanediyl group of which the two terminal atoms are attached to the same (carbon) atom, thus forming a spiro ring system;

spirocycloalkene is a substituent consisting of an alkenediyl group of which the two terminal atoms are attached to the same (carbon) atom, thus forming a spiro ring system;

the prefixes (1-4C), (2-4C) etc. have the usual meaning to restrict the meaning of the indicated group to those with 1 through 4, 2 through 4 etc. carbon atoms;

halogen refers to fluorine, chlorine, bromine and iodine;

spirocycloalkanone is a spirocycloalkane ring where one of the carbon atoms is forming a carbonyl group;

spirocycloalkenone is a spirocycloalkene ring where one of the carbon atoms is forming a carbonyl group.

The progestagen receptor affinity and efficacy of the compounds according to the invention make them suitable for use in control of fertility and reproduction, e.g. in female contraception, and further for female HRT, the treatment of gynaecological disorders, as components of male contraception and in diagnostic methods focussed on the amount and/or location of progesterone receptors in various tissues. For the latter purpose it can be preferred to make isotopically labelled variants of the compounds according to the invention.

The compounds of the invention may further be useful for the treatment of endometriosis, menorrhagia, menometrorrhagia, dysmenorrhoea, acne, fibroids, osteoporosis as well as other bone disorders, bone fraction repair, sarcopenia, frailty, skin ageing, female sexual dysfunction, postmenopausal symptoms, atherosclerosis, aplastic anaemia, lipodystrophy, side effects of chemotherapy, tumours (located in e.g. breast, ovary or uterus) and others.

The compounds of the invention may be administered in conjunction with estrogens, androgens, progestagens, antiprogestagens, and other suitable compounds such as folic acid, vitamins, minerals etc.

Methods to determine receptor binding as well as in vitro and in vivo assays to determine biological activity of the compounds are well known. In general, expressed receptor (or a functional part thereof) is treated with a compound of the invention and binding or stimulation or inhibition of a functional response is measured.

To measure a functional response, isolated DNA encoding the progesterone receptor gene, preferably the human receptor, is expressed in suitable host cells. Such a cell might be the Chinese Hamster Ovary (CHO) cell, but other cells are also suitable. Preferably the cells are of mammalian origin. Methods to construct recombinant progesterone receptor-expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein.

Techniques for site-directed mutagenesis, ligation of additional sequences, PCR, and construction of suitable expression systems are all by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided through the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with a compound of the invention to observe binding, or stimulation or inhibition of a functional response.

Alternatively, isolated cytosol containing the expressed receptor may be used to measure binding of a compound of the invention.

For measurement of binding, radioactive or fluorescence-labelled compounds may be used. As reference compound, the native hormone, or other compounds binding to the receptor, can be used. As an alternative, competition binding assays can be performed as well. Another assay involves screening for progesterone receptor mixed agonist/antagonist compounds of the invention by determining regulation of receptor-mediated natural target gene mRNA, i.e. genes regulated by the receptor through binding of the receptor in the promoter region of the gene. The levels of target gene mRNA will be reduced or increased, depending on the inhibitory or stimulating effect of a compound of the invention upon binding to the receptor.

In addition to direct measurement of mRNA levels in the exposed cells, cells can be used which in addition to transfection with receptor encoding DNA have also been transfected with a second DNA encoding a reporter gene, the expression of which responds to binding of the receptor towards responsive elements in the promoter of the particular reporter gene. Such responsive elements might be classical hormone-responsive elements, well known in the art and described e.g. in Beato, M, Chalepakis, G, Schauer, M, Slater, EP J. Steroid Biochem. 5 (1989)737-47 or might be constructed in such a way that they are connected to novel responsive elements. In general, reporter gene expression might be controlled by any response element reacting to progesterone receptor binding. Suitable reporter genes are e.g. LacZ, alkaline phosphatase, firefly luciferase and green fluorescence protein.

For selecting compounds of the subject invention with a mixed modulating effect on the progesterone receptor, testing in the agonistic mode must result in an intrinsic activity of between about 15% and about 85% of the maximal activity when (16α)-16-ethyl-21-hydroxy-19-norpregn-4-ene-3,20-dione is used as a reference. Moreover, this maximal agonistic activity should be reached at a concentration of $10^{-6}$ or less, and preferably at a concentration of $10^{-8}$ or less.

In the antagonistic mode, testing must result in an intrinsic activity of between about 85% and about 15% of the maximal activity when (6β,11β,17β)-11-[4-(dimethylamino)phenyl]-4',5'-dihydro-6-methylspiro[estra-4,9-diene-17,2'(3'H)-furan]-3-one is used as a reference.

An additional criterion is the $IC_{50}$ value, which must be $<10^{-6}$ M, preferably $<10^{-8}$ M. It will be understood by those skilled in the art that for the present invention compounds with a mixed P/AP profile are understood to have a profile ranging from a combination of minimal intrinsic agonistic activity of about 15% and maximal intrinsic antagonistic activity of about 85% to a combination of maximal intrinsic agonistic activity of about 85% and minimal intrinsic antagonistic activity of about 15%. Those skilled in the art will also recognize that, due to the biological variation in the assay, it is not always necessarily the case that the intrinsic agonistic activity and the intrinsic antagonistic activity add up to exactly 100%.

The skilled artisan will further recognize that desirable $EC_{50}$ and $IC_{50}$ values are dependent on the compound of the invention which is being tested. For example, a compound with an $EC_{50}$ which is less than $10^{-6}$ M is, generally, considered a candidate for drug selection. Preferably this value is lower than $10^{-8}$ M. However, a compound which has a higher $EC_{50}$ and/or $IC_{50}$, but has a suitable selectivity (or a combination of agonistic and antagonistic selectivity) for the particular receptor, may still be a candidate for drug selection.

Basically any transactivation assay in mammalian cells (cell line or primary culture) that can yield information about the possible receptor activation can be used for the purpose of selecting potent and suitable ligands. The added value of using several cell systems, with cells which originate from different organs, will be that information on the potential tissue specificity of the ligands is obtained. Without limitation, examples of cells frequently used to this end are, besides CHO cells, e.g. T47D cells, MCF7 cells, ECC-1 cells, HeLa cells, primary cultures of endometrial cells, and pituitary cells.

Suitable routes of administration for the compounds of the subject invention (also called active ingredient) are oral, rectal, nasal, topical (including transdermal, buccal and sublingual), vaginal or parenteral (including subcutaneous, intramuscular, intravenous and intradermal) administration or administration via an implant. In a specific embodiment, the compounds can be administered orally. The exact dose and regimen of administration of the active ingredient, or a pharmaceutical composition thereof, will necessarily be dependent upon the therapeutic effect to be achieved (e.g. contraception, HRT, endometriosis) and may vary with the particular compound, the route of administration, and the age and condition of the individual subject to whom the medicament is to be administered.

In general, parenteral administration requires lower dosages than other methods of administration which are more dependent upon adsorption. However, a dosage for humans is likely to contain 0.0001-25 mg per kg body weight. The desired dose may be presented as one dose or as multiple sub-doses administered at appropriate intervals throughout the day, or, in case of female recipients, as doses to be administered at appropriate (daily) intervals throughout the menstrual cycle.

The present invention thus also relates to pharmaceutical compositions comprising a compound according to Formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant The compositions may be prepared by methods known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredient(s), include those conventional in the art (Gennaro, supra), such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for the use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. Compositions or formulations suitable for administration by nasal inhalation include fine dusts or mists which may be generated by means of metered dose pressurized aerosols, nebulisers or insufflators.

The compounds of the invention can also be administered in the form of devices consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in EP 303,306.

The compounds of the invention can also be administered in the form of a vaginal ring such as described for example in EP 876815.

The compounds of the invention can be produced by various methods known in the art of organic chemistry in general. More specifically the routes of synthesis as illustrated in the previous and following schemes and examples can be used. In the schemes and examples the following abbreviations are used:

THF: tetrahydrofuran
DMF: N,N-dimethylformamide
$NaHCO_3$: sodium hydrogencarbonate
$NH_4Cl$: ammonium chloride
$Na_2S_2O_3$: sodium thiosulfate
$SiO_2$: silicon dioxide (silica gel)
$Na_2SO_4$: sodium sulfate
$MgSO_4$: magnesium sulfate
LCMS: liquid chromatography/mass spectrometry
HPLC: high performance liquid chromatography
NMR: nuclear magnetic resonance
M: molar The present invention is further described in the following examples which are not in any way intended to limit the scope of the invention as claimed.

EXAMPLES

Example 1

Preparation of (11β,16α,17β)-17-cyclopropylcarbonyl-16-methyl-11-[4-(3-pyridinyl)-phenyl]estra-4,9-dien-3-one a. 17-[[(Trifluoromethyl)sulfonyl]oxy]estra-5(10),9(11),16-trien-3-one cyclic 1,2-ethanediyl acetal Lithium hexamethyldisilazane (1M in THF, 478 mL, 478 mmol) was added to THF (1 L) and cooled to −40° C. under a nitrogen atmosphere. A solution of estra-5(10),9(11)-diene-3,17-dione cyclic 3-(1,2-ethanediyl acetal) (50 g, 159 mmol) in dry THF (500 mL) was added dropwise while the reaction temperature slowly raised until −15° C. After stirring 30 minutes at −15° C., N-phenyl-bis(trifluoromethanesulfonimide) (62.5 g, 175 mmol) was added batchwise and the reaction mixture was stirred for 3 hours at 0° C. A saturated aqueous $NaHCO_3$ solution was added dropwise (exothermic) followed by water. The organic layer was separated and the aqueous layer was extracted three times with ethyl acetate. The combined organic layers were washed with brine, dried ($Na_2SO_4$) and evaporated to dryness. The crude product was purified by column chromatography ($SiO_2$, heptane/ethyl acetate, 4/1) to give 17-[[(trifluoromethyl)sulfonyl]oxy]estra-5(10),9(11),16-trien-3-one cyclic 1,2-ethanediyl acetal (90.1 g, 159 mmol, 100% yield, still containing some solvent). $^1H$ NMR (400 MHz, $CDCl_3$): δ 0.91 (s, 3H), 1.20-2.55 (m, 16H), 3.98 (s, 4H), 5.52 (m, 1H), 5.59 (m, 1H).

b. N-methoxy-N-methyl-3,3-[1,2-ethanediylbis (oxy)]oxo-estra-5(10),9(11),16-triene-17-carboxamide Triethylamine (221 mL, 1.59 mol), triphenylphosphine (6.67 g, 25 mmol) and N,O-dimethylhydroxylamine.HCl (82.2 g, 843 mmol) were added to a solution of 17-[[(trifluoromethyl)sulfonyl]oxy]estra-5(10),9(11),16-trien-3-one cyclic 1,2-ethanediyl acetal (70.9 g, 159 mmol) in DMF (1.5 L). Carbon monoxide was passed through the solution for 10 minutes, then palladium(II)acetate (2.86 g, 12.7 mmol) was added and the reaction mixture was stirred overnight at 60° C. under a CO atmosphere. The reaction mixture was poured into a saturated aqueous $NH_4Cl$ solution and extracted three times with ethyl acetate. The combined organic layers were washed with brine, dried ($Na_2SO_4$) and evaporated to dryness. The crude product was purified by column chromatography ($SiO_2$, heptane/ethyl acetate, 2/1) to give N-methoxy-N-methyl-3,3-[1,2-ethanediylbis(oxy)]estra-5(10),9(11),16-triene-17-carboxamide (59.7 g, 139 mmol, 87% yield, still containing some solvent). $^1$H NMR (400 MHz, $CDCl_3$): δ 0.97 (s, 3H), 1.25-2.58 (m, 16H), 3.25 (s, 3H), 3.62 (s, 3H), 3.99 (s, 4H), 5.58 (m, 1H), 6.41 (m, 1H).

c. 17-(Cyclopropylcarbonyl)estra-5(10),9(11),16-trien-3-one cyclic 1,2-ethanediyl acetal A solution of cyclopropyl bromide (22.3 mL, 278 mmol) in diethyl ether (20 mL) was slowly added to a cooled suspension (0° C.) of crushed lithium (5.8 g, 834 mmol) in ether (380 mL) (exothermic) under a nitrogen atmosphere. The reaction mixture was stirred for 90 minutes while the temperature rose to room temperature. The solution of this lithiate was slowly added to a cooled solution (0° C.) of N-methoxy-N-methyl-3,3-[1,2-ethanediylbis(oxy)]estra-5(10),9(11),16-triene-17-carboxamide (59.7 g, 139 mmol) in THF (260 mL). After stirring this mixture for 2 hours at 0° C., a saturated aqueous $NH_4Cl$ solution was added dropwise (exothermic) followed by water. The organic layer was separated and the aqueous layer was extracted three times with ethyl acetate. The combined organic layers were washed with brine, dried ($Na_2SO_4$) and evaporated to dryness. The crude product was purified by column chromatography ($SiO_2$, heptane/ethyl acetate, 4/1) to give 17-(cyclopropylcarbonyl)estra-5(10),9(11),16-trien-3-one cyclic 1,2-ethanediyl acetal (33.9 g, 93 mmol, 67% yield). $^1$H NMR (400 MHz, $CDCl_3$): δ 0.82-2.67 (m, 24H), 3.99 (s, 4H), 5.59 (m, 1H), 6.88 (m, 1H).

d. (16α,17β)-17-(Cyclopropylcarbonyl)-16-methylestra-5(10),9(11)-dien-3-one cyclic 1,2-ethanediyl acetal Methylmagnesium chloride (3M in THF, 92.6 mL, 278 mmol) was added to a stirred and cooled solution (0° C.) of copper(II)acetate (1.7 g, 9.3 mmol) in THF (1 L) under a nitrogen atmosphere. A solution of 17-(cyclopropylcarbonyl)estra-5(10),9(11),16-trien-3-one cyclic 1,2-ethanediyl acetal (33.9 g, 93 mmol) and trimethylsilyl chloride (58.5 mL, 463 mmol) in THF (500 mL) was added dropwise while the temperature was kept at 0° C. After 1 hour another equivalent of methylmagnesium chloride was added dropwise and stirring was continued for 30 minutes at 0° C. A saturated aqueous $NH_4Cl$ solution was added dropwise followed by water. The organic layer was separated and the aqueous layer was extracted three times with ethyl acetate. The combined organic layers were washed with brine, dried ($Na_2SO_4$) and evaporated to dryness to give (16α,17β)-17-(cyclopropylcarbonyl)-16-methylestra-5(10),9(11)-dien-3-one cyclic 1,2-ethanediyl acetal (32.9 g, 86 mmol 93% yield). $^1$H NMR (400 MHz, $CDCl_3$): δ 0.61 (s, 3H), 0.80-2.79 (m, 26H), 3.99 (s, 4H), 5.55 (m, 1H).

e. (5α,10α,16α,17β)-17-(Cyclopropylcarbonyl)-5,10-epoxy-16-methylestr-9(11)-en-3-one cyclic 1,2-ethanediyl acetal To a stirred solution of (16α,17β)-17-(cyclopropylcarbonyl)-16-methylestra-5(10),9(11)-dien-3-one cyclic 1,2-ethanediyl acetal (32.9 g, 86 mmol) in dichloromethane (500 mL), pyridine (2.1 mL, 26.7 mmol), trifluoroacetophenone (12.1 mL, 86.1 mmol) and hydrogen peroxide (30% in water, 96.1 mL) were added. The resulting two-phase system was vigorously stirred at ambient temperature for 2 days. The organic layer was separated and the aqueous layer was extracted twice with dichloromethane. The combined organic layers were washed twice with a saturated aqueous $Na_2S_2O_3$ solution, washed with brine, dried ($Na_2SO_4$) and evaporated to dryness. The crude product was purified by column chromatography ($SiO_2$, heptane/ethyl acetate, 5/1) to give (5α,10α,16α,17β)-17-(cyclopropylcarbonyl)-5,10-epoxy-16-methylestr-9(11)-en-3-one cyclic 1,2-ethanediyl acetal (27.9 g, 70.1 mmol, 81% yield, 16% β-epoxide present). $^1$H NMR (400 MHz, $CDCl_3$): δ 0.61 (s, 3H), 0.81-2.78 (m, 26H), 3.87-3.96 (m, 4H), 6.02 (m, 1H).

f. (5α,11β,16α,17β)-11-(4-Bromophenyl)-17-(cyclopropylcarbonyl)-5-hydroxy-16-methylestr-9-en-3-one cyclic 1,2-ethanediyl acetal A grain of iodine was added to magnesium (8.4 g, 350 mmol) and heated for 1 minute. A solution of 1,4-dibromobenzene (85.1 g, 350 mmol) and a few drops of 1,2-dibromoethane in THF (400 mL) was added dropwise under a nitrogen atmosphere while the temperature was kept at 45° C. After 1 hour stirring at 45° C. this Grignard suspension was added to a cooled (−40° C.) solution of (5α,10α,16α,17β)-17-(cyclopropylcarbonyl)-5,10-epoxy-16-methylestr-9(11)-en-3-one cyclic 1,2-ethanediyl acetal (27.9 g, 70.1 mmol) and copper(I) chloride (3.4 g, 35.1 mmol) in 1THF (550 mL) under a nitrogen atmosphere while the temperature was kept at −40° C. The reaction mixture was stirred for 2 hours while the temperature rose to room temperature. A saturated aqueous $NH_4Cl$ solution was added dropwise (exothermic) followed by water. The organic layer was separated and the aqueous layer was extracted three times with ethyl acetate. The combined organic layers were washed with a saturated aqueous $NaHCO_3$ solution and brine, dried ($Na_2SO_4$) and evaporated to dryness. The crude product was purified by column chromatography ($SiO_2$, heptane/ethyl acetate, 2/1) to give (5α,11β,16α,17β)-11-(4-bromophenyl)-17-(cyclopropylcarbonyl)-5-hydroxy-16-methylestr-9-en-3-one cyclic 1,2-ethanediyl acetal (30.0 g, 54.1 mmol, 77% yield). $^1$H NMR (400 MHz, $CDCl_3$): δ 0.24 (s, 3H), 0.80-2.71 (m, 26H), 3.89-4.05 (n, 4H), 4.23 (d, J=6 Hz, 1H), 4.37 (d, J=1 Hz, 1H), 7.05-7.09, (m, 2H), 7.35-7.38 (m, 2H).

g. (11β,16α,17β)-11-(4-bromophenyl)-17-cyclopropylcarbonyl-16-methylestra-4,9-dien-3-one 2 N Hydrochloric acid (81.1 mL, 162 mmol) was added to a solution of (5α,11β,16α,17β)-11-(4-bromophenyl)-17-(cyclopropylcarbonyl)-5-hydroxy 16-methylestr-9-en-3-one cyclic 1,2-ethanediyl acetal (30.0 g, 54.1 mmol) in acetone (600 mL). After stirring this solution for 10 minutes at room temperature, a saturated aqueous NaHCO₃ solution was added. The reaction mixture was extracted three times with ethyl acetate. The combined organic layers were washed with brine, dried (Na₂SO₄) and evaporated to dryness. The crude product was purified by column chromatography (SiO₂, heptane/ethyl acetate, 2/1) to give (11β,16α,17β)-11-(4-bromophenyl)-17-cyclopropylcarbonyl-16-methylestra-4,9-dien-3-one (17.6 g, 35.7 mmol, 66% yield). $^1$H NMR (400 MHz, CDCl₃): δ 0.30 (s, 3H), 0.84-2.76 (m, 24M), 4.34 (d, J=8 Hz, 1H), 5.79 (s, 1H), 7.02-7.05 (m, 2H), 7.37-7.41 (m, 2H).

h. (11β,16α,17β)-17-cyclopropylcarbonyl-16-methyl-11-[4-(3-pyridinyl)phenyl]estra-4,9-dien-3-one (11β,16α,17β)-11-(4-Bromophenyl)-17-cyclopropylcarbonyl-16-methylestra-4,9-dien-3-one (10 g, 20.3 mmol), 3-pyridinylboronic acid (3.7 g, 30.4 mmol), potassium phosphate (5.2 g, 24.3 mmol), bis(triphenylphosphine)palladium (II) chloride (442 mg, 0.61 mmol) and triphenylarsine (426 mg, 1.4 mmol) were dissolved in a mixture of dioxane (240 mL) and water (30 mL) under a nitrogen atmosphere. The reaction mixture was stirred for 2 hours at 100° C. and then cooled to room temperature. Water was added and the mixture was extracted three times with ethyl acetate. The combined organic layers were washed with brine, dried (MgSO₄) and evaporated to dryness. Purification by column chromatography (SiO₂, heptane/ethyl acetate, gradient 2/1 to 1/2) gave crude product (8.3 g, 16.9 mmol) which was crystallized from acetonitrile/water to give (11β,16α,17β)-17-cyclopropylcarbon-yl-16-methyl-11-[4-(3-pyridinyl)phenyl]estra-4,9-dien-3-one (5.5 g, 11.2 mmol, 55% yield), mp. 206° C. $^1$H NMR (400 MHz, CDCl₃): δ 0.35 (s, 3H), 0.86-2.86 (m, 24H), 4.46 (d, J=8 Hz, 1H), 5.80 (s, 1H), 7.26-7.29 (m, 2H), 7.35 (dd, J=10 and 6 Hz, 1H), 7.49-7.53 (m, 2H), 7.86 (dt, J=10 and 4 Hz, 1H), 8.57 (dd, J=6 and 4 Hz, 1H), 8.84 (d, J=4 Hz, 1H).

Example 2

Preparation of (11β,16α,17β)-17-cyclopropylcarbonyl-16-methyl-11-[4-(3-pyridinyl)-phenyl]estra-4,9-dien-3-one hydrochloride To a solution of (11β,16α,17β)-17-cyclopropylcarbonyl-16-methyl-11-[4-(3-pyridinyl)phenyl]estra-4,9-dien-3-one (40 mg, 0.081 mmol) in acetonitrile (1 mL) were added 2 N hydrochloric acid (40 µL) and water (5 mL). Lyophilisation of this mixture gave 11β,16α,17β)-17-cyclopropylcarbonyl-16-methyl-11-[4-(3-pyridinyl)phenyl]estra-4,9-dien-3-one hydrochloride in quantitative yield (40 mg, 0.08 mmol). $^1$H NMR (400 MHz, CDCl₃): δ 0.34 (s, 3H), 0.80-2.85 (m, 24H), 4.47 (d, J=7 Hz, 1H), 5.81 (s, 1H), 7.31-7.35 (m, 2H), 7.51-7.55 (m, 2H), 7.64 (dd, J=8 and 5 Hz, 1H), 8.18 (dt, J=8 and 1 Hz, 1H), 8.62 (d, J=5 Hz, 1H), 8.90 (d, J=1 Hz, 1H).

Example 3

Preparation of (11β,16α,17β)-17-cyclopropylcarbonyl-11-[4-(6-methoxypyridin-3-yl)phenyl]-16-methylestra 4,9-dien-3-one Reaction of (11β,16α,17β)-11-(4-bromophenyl)-17-cyclopropylcarbonyl-16-methylestra-4,9-dien-3-one and 6-methoxy-3-pyridinylboronic acid using the procedure described in example 1 step h afforded the title compound (54% yield). $^1$H NMR (400 MHz, CDCl₃): δ 0.35 (s, 3H), 0.84-0.99 (m, 6H), 1.08-1.15 (m, 1H), 1.33-1.39 (m, 1H), 1.45-1.54 (m, 1H), 1.62-1.70 (m, 2H), 1.91-1.97 (m, 1H), 2.01-2.08 (m, 1H), 2.24-2.53 (m, 6H), 2.58-2.64 (m, 2H), 2.68-2.85 (m, 3H), 3.98 (s, 3H), 4.44 (d, J=8 Hz, 1H), 5.80 (s, 1H), 6.80 (d, J=8 Hz, 1H), 7.23 (d, J=7 Hz, 2H), 7.44 (d, J=7 Hz, 2H), 7.75-7.79 (m, 1H), 8.36-8.38 (m, 1H).

Example 4

Preparation of (11β,16α,17β)-11-[4-(6-chloropyridin-3-yl)phenyl]-17-cyclopropyl-carbonyl-16-methylestra-4,9-dien-3-one To prepare the title compound from (11β,16α,17β)-11-(4-bromophenyl)-17-cyclopropylcarbonyl-16-methylestra-4,9-dien-3-one and 6-chloro-3-pyridinylboronic acid the procedure described in example 1 step h was slightly modified The reaction mixture was heated for 4 hours and an additional 2 equivalents of 6-chloro-3-pyridinylboronic acid were added in 4 portions. Purification by LCMS followed by lyophilisation gave the product (11% yield). $^1$H NMR (400 MHz, CDCl₃): δ 0.34 (s, 3H), 0.84-2.84 (m, 24H), 4.45 (d, J=7 Hz, 1H), 5.80 (s, 1H), 7.25-7.30 (m, 2H), 7.38 (d, J=8 Hz, 1H), 7.45-7.49 (m, 2H), 7.82 (dd, J=8 and 3 Hz, 1H), 8.59 (d, J=3 Hz, 1H).

Example 5

Preparation of (11β,16α,17β)-17-cyclopropylcarbonyl-11-[4-(6-fluoropyridin-3-yl)phenyl]-16-methylestra-4,9-dien-3-one (11β,16α,17β)-11-(4-Bromophenyl)-17-cyclopropylcarbonyl-16-methylestra-4,9-dien-3-one and 6-fluoro-3-pyridinylboronic acid were used as described in example 1 step h. Purification by LCMS followed by lyophilisation gave the product (65% yield). $^1$H NMR (400 MHz, CDCl₃): δ 0.34 (s, 3H), 0.80-2.85 (m, 24H), 4.45 (d, J=7 Hz, 1H), 5.80 (s, 1H), 7.00 (dd, J=8 and 3 Hz, 1H), 7.25-7.29 (m, 2H), 7.44-7.48 (m, 2H), 7.95 (dt, J=8 and 3 Hz, 1H), 8.41 (d, J=3 Hz, 1H).

Example 6

Preparation of (11β,16α,17β)-17-cyclopropylcarbonyl-16-methyl-11-[4-(5-methoxy-pyridin-3-yl)phenyl]estra-4,9-dien-3-one (11β,16α,17β)-11-(4-Bromophenyl)-17-cyclopropylcarbonyl-16-methylestra-4,9-dien-3-one and 5-methoxy-3-pyridinylboronic acid were used as described in example 1 step h. Purification by LCMS followed by lyophilisation gave the product (41% yield). $^1$H NMR (400 MHz, CDCl₃): δ 0.35 (s, 3H), 0.80-2.86 (m, 24H), 3.92 (s, 3H), 4.46 (d, J=7 Hz, 1H), 5.80 (s, 1H), 7.24-7.29 (m, 2H), 7.35 (dd, J=3 and 1 Hz, 1H), 7.48-7.53 (m, 2H), 8.28 (d, J=3 Hz, 1H), 8.45 (d, J=1 Hz, 1H).

Example 7

Preparation of (11β,16α,17β)-17-cyclopropylcarbonyl-16-methyl-11-[4-(3-quinolidinyl)phenyl]estra-4, 9-dien-3-one (11β,16α,17β)-11-(4-Bromophenyl)-17-cyclopropylcarbonyl-16-methylestra-4,9-dien-3-one and quinoline-3-boronic acid pinacolate were heated for 3 hours according to the procedure described in example 1 step h. Purification by LCMS followed by lyophilisation gave the title compound (18% yield). $^1$H NMR (400 MHz, CDCl₃): δ 0.38 (s, 3H), 0.78-2.89 (m, 24H), 4.49 (d, J=7 Hz, 1H), 5.81 (s, 1H), 7.30-7.34 (m, 2H), 7.58 (dt, J=7 and 1 Hz, 1H), 7.63-7.67 (m, 2H), 7.72 (dt, J=8 and 1 Hz, 1H), 7.87 (dd, J=8 and 1 Hz, 1H), 8.13 (d, J=8 Hz, 1H), 8.29 (d, J=3 Hz, 1H), 9.17 (d, J=3 Hz, 1H).

Example 8

Preparation of (11β,16α,17β)-17-cyclopropylcarbonyl-16-methyl-11-[4-(4-pyridazinyl)phenyl]estra-4,9-dien-3-one n-Butyllithium (2.76 mL, 6.9 mmol, 2.5 M in hexane) was added dropwise to a cooled (0° C.) solution of diisopropylamine (0.97 mL, 6.9 mmol) in tetrahydrofuran (2 mL) under a nitrogen atmosphere. After stirring for 30 minutes the reaction mixture was cooled to −78° C. and a solution of pyridazine (452 μL, 6.3 mmol) and tributyltin chloride (1.9 mL, 6.9 mmol) were added simultaneously while the temperature was kept below −70° C. The reaction mixture was stirred for 2 hours at −78° C.; subsequently, a saturated aqueous NH$_4$Cl solution was added and the reaction mixture was extracted three times with ethyl acetate. The combined organic layers were dried (MgSO$_4$) and evaporated to dryness. The crude product was purified by LCMS to give tributylstannylpyridazine (197 mg, 0.53 mmol, 8% yield). This stannylpyridazine (183 mg, 0.49 mmol), (11β,16α,17β)-11-(4-bromophenyl)-17-cyclopropylcarbonyl-16-methylestra-4,9-dien-3-one (100 mg, 0.20 mmol) and bis(triphenylphosphine)palladium(II) chloride (3 mg, 0.004 mmol) were dissolved in dioxane (3 mL) under a nitrogen atmosphere. The reaction mixture was stirred overnight at 110° C. and then cooled to room temperature. Water was added and the mixture was extracted three times with dichloromethane. The combined organic layers were dried through a phase separate filter and evaporated to dryness. Purification by LCMS followed by lyophilisation gave (11β,16α,17β)-17-cyclopropylcarbonyl-16-methyl-11-[4-(4-pyridazinyl)phenyl]estra-4,9-dien-3-one (78 mg, 0.16 mmol, 79% yield). $^1$H NMR (400 MHz, CDCl$_3$): δ 0.33 (s, 3H), 0.85-2.84 (m, 26H), 4.48 (d, J=7 Hz, 1H), 5.81 (s, 1H), 7.33-7.37 (m, 2H), 7.60-7.64 (m, 3H), 9.21 (dd, J=5 and 1 Hz, 1H), 9.46 (dd, J=3 and 1 Hz, 1H).

The same title compound was also obtained using 4-tributylstannylpyridazine prepared according to the procedures described in Eur. J. Org. Chem. 2885-2896 (1998) and Tetrahedron Letters 38, 5791-5794 (1997).

Example 9

Preparation of (11β,16α,17β)-17-cyclopropylcarbonyl-16-methyl-11-[4-(pyrazin-2-yl)phenyl]estra-4,9-dien-3-one According to the procedure described in example 8, (11β,16α,17β)-11-(4-bromophenyl)-17-cyclopropylcarbonyl-16-methylestra-4,9-dien-3-one and 2-tributylstannylpyrazine were heated in a microwave at 135° C. (150 W, 25 minutes) to give the title compound (35% yield). $^1$H NMR (400 MHz, CDCl$_3$): δ 0.33 (s, 3H), 0.84-2.86 (m, 24H), 4.47 (d, J=7 Hz, 1H), 5.81 (s, 1H), 7.30-7.34 (m, 2H), 7.92-7.96 (m, 2H), 8.49 (d, J=3 Hz, 1H), 8.61 (dd, J=3 and 1 Hz, 1H), 9.01 (d, J=1 Hz, 1H).

Example 10

Preparation of (11β,16α,17β)-17-cyclopropylcarbonyl-16-methyl-11-[4-(2-pyridinyl)phenyl]estra-4,9-dien-3-one (PPh$_3$)$_2$PdCl$_2$ (4 mg, 0.006 mmol), ferrocene palladium dichloride (6 mg, 0.009 mmol) and 2-pyridylzinc bromide (2 mL, 1.0 mmol) were added to a solution of (11β,16α,17β)-11-(4-bromophenyl)-17-cyclopropylcarbonyl-16-methylestra-4,9-dien-3-one (200 mg, 0.41 mmol) in THF (4 mL) under a nitrogen atmosphere. The reaction mixture was stirred for 5 hours at 60° C. and then cooled to room temperature. A saturated aqueous NH$_4$Cl solution was added and the mixture was extracted three times with dichloromethane. The combined organic layers were dried through a phase separate filter and evaporated to dryness. Purification by HPLC followed by lyophilisation gave (11β,16α,17β)-17-cyclopropylcarbonyl-16-methyl-11-[4-(2-pyridinyl)phenyl]estra-4,9-dien-3-one (80 mg, 0.16 mmol, 40% yield). $^1$H NMR (400 MHz, CDCl$_3$): δ 0.33 (s, 3H), 0.80-2.87 (m, 24H), 4.46 (d, J=7 Hz, 1H), 5.80 (s, 1H), 7.20-7.23 (m, 1H), 7.25-7.29 (m, 2H), 7.68-7.77 (m, 2H), 7.89-7.92 (m, 2H), 8.67 (dt, J=5 and 1 Hz, 1H).

Example 11

Preparation of (11β,16α,17β)-17-cyclopropylcarbonyl-16-methyl-11-[4-(5 methylpyridin-2-yl)phenylestra-4,9-dien-3-one The title compound (10% yield) was prepared from (11β,16α,17β)-11-(4-bromophenyl)-17-cyclopropylcarbonyl-16-methylestra-4,9-dien-3-one and 5-methyl-2-pyridinylzinc bromide using the procedure described in example 10. $^1$H NMR (400 MHz, CDCl$_3$): δ 0.33 (s, 3H), 0.80-2.86 (m, 27H), 4.45 (d, J=7 Hz, 1H), 5.79 (s, 1H), 7.22-7.26 (m, 2H), 7.52-7.60 (m, 2H), 7.85-7.88 (m, 2H), 8.48-8.50 (m, 1H).

Example 12

Preparation of (11β,16α,17β)-17-cyclopropylcarbonyl-16-methyl-11-[4-(4-pyridinyl)phenyl]estra-4,9-dien-3-one (11β,16α,17β)-11-(4-Bromophenyl)-17-cyclopropylcarbonyl-16-methylestra-4,9-dien-3-one and 4-pyridinylboronic acid were applied as described in example 1 step h. Purification by HPLC followed by crystallisation (acetonitrile/water) gave the product (44% yield). $^1$H NMR (400 MHz, CDCl$_3$): δ 0.33 (s, 3H), 0.84-2.85 (m, 24H), 4.46 (d, J=7 Hz, 1H), 5.81 (s, 1H), 7.26-7.30 (m, 2H), 7.48-7.50 (m, 2H), 7.55-7.59 (m, 2H), 8.63-8.65 (m, 2H).

Example 13

Preparation of (11β,16α,17β)-17-cyclopropylcarbonyl-16-ethenyl-11-[4-(3-pyridinyl)phenyl]estra-4,9-dien-3-one a. (16α,17β)-17-(Cyclopropylcarbonyl)-16-ethenylestra-5(10),9(11)-dien-3-one cyclic 1,2-ethanediyl acetal Reaction of 17-(cyclopropylcarbonyl)estra-5(10),9(11),16-trien-3-one cyclic 1,2-ethanediyl acetal and vinylmagnesium chloride according to the procedure described in example 1 step d afforded the title compound (48% yield). $^1$H NMR (400 MHz, CDCl$_3$): δ 0.63 (s, 3H), 0.80-2.66 (m, 21H), 2.71 (d, J=9 Hz, 1H), 3.30-3.39 (m, 1H), 3.99 (s, 4H), 4.84-4.97 (m, 2H), 5.54-5.58 (m, 1H), 5.71-5.81 (m, 1H).

b. (11β,16α,17β)-17-Cyclopropylcarbonyl-16-ethenyl-11-[4-(3-pyridinyl)phenyl]-estra-4,9-dien-3-one (16α,17β)-17-(Cyclopropylcarbonyl)-16-ethenylestra-5(10),9(11)-dien-3-one cyclic 1,2-ethanediyl acetal was transformed into crude title compound using the procedures described in example 1 steps e, f, g and h. Purification by preparative LCMS followed by lyophilisation gave the title compound. (15% yield over these 4 steps). ¹H NMR (400 MHz, CDCl₃): δ 0.38 (s, 3H), 0.84-0.99 (m, 3H), 1.08-1.15 (m, 1H), 1.46-2.88 (m, 16H), 3.26-3.35 (m, 1H), 4.47 (d, J=7 Hz, 1H), 4.86-4.97 (m, 2H), 5.70-5.79 (m, 1H), 5.81 (s, 1H), 7.26-7.30 (m, 2H), 7.35 (dd, J=8 and 5 Hz, 1H), 7.49-7.53 (m, 2H), 7.86 (dt, J=8 and 1 Hz, 1H), 8.58 (dd, J=5 and 1 Hz, 1H), 8.84 (d, J=1 Hz, 1H).

Example 14

Preparation of [11β,16α(E),17β]-17-cyclopropylcarbonyl-16-(2-phenylethenyl)-11-[4-(3-pyridinyl)phenyl]estra-4,9-dien-3-one In the purification of (11β,16α,17β)-17-cyclopropylcarbonyl-16-ethenyl-11-[4-(3-pyridinyl)phenyl]estra-4,9-dien-3-one the title compound was isolated as a by-product (2% yield). ¹H NMR (400 MHz, CDCl₃): δ 0.41 (s, 3H), 0.83-1.15 (m, 4H), 1.50-2.91 (m, 16H), 3.43-3.53 (m, 1H), 4.49 (d, J=7 Hz, 1H), 5.82 (s, 1H), 6.12 (dd, J=16 and 8 Hz, 1H), 6.32 (d, J=16 Hz, 1H), 7.17-7.22 (m, 1H), 7.26-7.40 (m, 7H), 7.50-7.54 (m, 2H), 7.85-7.91 (m, 1H), 8.56-8.61 (m, 1H), 8.83-8.87 (m, 1H).

Example 15

Preparation of (11β,16α,17β)-17-(cyclopropylcarbonyl)-16-ethenyl-11-[4-(6-methoxypyridin-3-yl)phenyl]estra-4,9-dien-3-one (16α,17β)-17-(Cyclopropylcarbonyl)-16-ethenylestra-5(10),9(11)-dien-3-one cyclic 1,2-ethanediyl acetal was transformed into crude title compound using the procedures described in example 1 steps e, f, g and h (using 6-methoxy-3-pyridinylboronic acid in the last step). Purification by crystallisation from heptane gave the title compound. (24% yield over these 4 steps), mp. 197° C. ¹H NMR (400 MHz, CDCl₃): δ 0.39 (s, 3H), 0.84-2.87 (m, 20H), 3.26-3.34 (m, 1H), 3.98 (s, 3H), 4.45 (d, J=7 Hz, 1H), 4.88 (d, J=11 Hz, 1H), 4.95 (d, J=16 Hz, 1H), 5.70-5.81 (m, 2H), 6.81 (d, J=8 Hz, 1H), 7.23 (d, J=8 Hz, 2H), 7.45 (d, J=8 Hz, 2H), 7.77 (dd, J=8 and 3 Hz, 1H), 8.37 (d, J=3 Hz, 1H).

Example 16

Preparation of (11β,16α,17β)-17-cyclopropylcarbonyl-16-ethyl-11-[4-(3-pyridinyl)-phenyl]-estra-4,9-dien-3-one a. (16α,17β)-17-(Cyclopropylcarbonyl)-16-ethyl-estra-5(10),9(11)-dien-3-one cyclic 1,2-ethanediyl acetal Reaction of 17-(cyclopropylcarbonyl)estra-5(10),9(11),16-trien-3-one cyclic 1,2-ethanediyl acetal and ethylmagnesium chloride according to the procedure described in example 1 step d afforded the title compound (87% yield). ¹H NMR (400 MHz, CDCl₃): δ 0.60 (s, 3H), 0.80-2.64 (m, 28H), 3.99 (s, 4H), 5.54-5.58 (m, 1H).

b. (11β,16α,17β)-17-Cyclopropylcarbonyl-16-ethyl-11-[4-(3-pyridinyl)phenyl]-estra-4,9-dien-3-one (16α,17β)-17-(Cyclopropylcarbonyl)-16-ethylestra-5(10),9(11)-dien-3-one cyclic 1,2-ethanediyl acetal was transformed into crude title compound using the procedures described in example 1 steps e, f, g and h. Purification by preparative LCMS followed by lyophilisation gave the title compound. (22% yield over these 4 steps). ¹H NMR (400 MHz, CDCl₃): δ 0.35 (s, 3H), 0.82 (t, 3=7 Hz, 3H), 0.87-0.98 (m, 3H), 1.07-1.14 (m, 1H), 1.25-1.34 (m, 2H), 1.41-1.64 (m, 5H), 1.91-1.99 (m, 1H), 2.03-2.11 (m, 1H), 2.24-2.85 (m, 10H), 4.46 (d, J=7 Hz, 1H), 5.80 (s, 1H), 7.25-7.30 (m, 2H), 7.35 (dd, J=7 and 5 Hz, 1H), 7.48-7.53 (m, 2H), 7.46 (dt, J=8 and 1 Hz, 1H), 8.57 (dd, J=5 and 1 Hz, 1H), 8.84 (d, J=3 Hz, 1H).

Example 17

Preparation of (11β,16α,17β)-17-cyclopropylcarbonyl-16-ethyl-11-[4-(6-methoxy-pyridin-3-yl)phenyl]-estra-4,9-dien-3-one (16α,17β)-17-(Cyclopropylcarbonyl)-16-ethylestra-5(10),9(11)-dien-3-one cyclic 1,2-ethanediyl acetal was transformed into crude title compound using the procedures described in example 1 steps e, f, g and h using 6-methoxy-3-pyridinylboronic acid in the last step. Purification by column chromatography gave the title compound. (14% yield over these 4 steps). δ 0.35 (s, 3H), 0.82 (t, J=8 Hz, 3H), 0.85-0.99 (m, 4H), 1.07-1.13 (m, 1H), 1.25-1.34 (m, 2H), 1.41-2.84 (m, 16H), 3.98 (s, 3H), 4.44 (d, J=7 Hz, 1H), 5.80 (s, 1H), 6.80 (d, J=8 Hz, 1H), 7.21-7.25 (m, 2H), 7.42-7.46 (m, 2H), 7.77 (dd, J=8 and 2 Hz, 1H), 8.37 (d, J=2 Hz, 1H).

Example 18

Preparation of (11β,17β)-17-cyclopropylcarbonyl-11-[4-(3-pyridinyl)phenyl]estra-4,9-dien-3-one a. (17β)-17-(Cyclopropylcarbonyl)estra-5(10),9(11)-dien-3-one cyclic 1,2-ethanediyl acetal K-selectride (1M in THF, 12.1 mL, 12.1 mmol) was added dropwise to a cooled solution (−78° C.) of 17-(cyclopropylcarbonyl)estra-5(10),9(11),16-trien-3-one cyclic 1,2-ethanediyl acetal (3.7 g, 10.0 mmol) in THF (105 mL) under a nitrogen atmosphere while the reaction temperature was kept below −70° C. After stirring this solution for 20 minutes, a saturated aqueous Na₂SO₄ solution was added dropwise followed by water. The organic layer was separated and the aqueous layer was extracted three times with ethyl acetate. The combined organic layers were washed with brine, dried (Na₂SO₄) and evaporated to dryness. The crude product was purified by column chromatography (SiO₂, heptane/ethyl acetate, 4/1) to give (17β)-17-(cyclopropylcarbonyl)estra-5(10),9(11)-dien-3-one cyclic 1,2-ethanediyl acetal (2.1 g, 5.8 mmol 57% yield). ¹H NMR (400 MHz, CDCl₃): δ 0.59 (s, 3H), 0.80-2.59 (m, 23H), 2.86 (t, J=9 Hz, 1H), 3.99 (s, 4H), 5.55-5.60 (m, 1H).

b. (17β)-17-(Cyclopropylhydroxymethyl)estra-5(10),9(11)-dien-3-one cyclic 1,2-ethanediyl acetal A solution of 17-(cyclopropylcarbonyl)estra-5(10),9(11)-dien-3-one cyclic (1,2-ethanediyl acetal) (2.1 g, 5.8 mmol) in diethyl ether (54 mL) was added slowly to a cooled (0° C.) suspension of lithium aluminum hydride (262 mg, 6.9 mmol) in diethyl ether (36 mL) under a nitrogen atmosphere. After 1 hour stirring at 0° C. a saturated aqueous Na₂SO₄ solution was added until the grey colour disappeared. Solid Na$_2$SO$_4$ was added and the mixture was filtered, washed with ethyl acetate and the filtrate evaporated to dryness to give cyclic (17β)-17-(cyclopropylhydroxymethyl)estra-5(10),9(11)-dien-3-one 1,2-ethanediyl acetal (2.2 g, 5.8 mmol, >100% yield, product still contained some ethyl acetate). $^1$H NMR (400 MHz, CDCl$_3$): δ 0.20-0.59 (m, 4H), 0.70 (s, 3H), 0.82-2.59 (m, 21H), 2.85 (dt, J=9 and 4 Hz, 1H), 3.99 (s, 4H), 5.53-5.58 (m, 1H).

c. (5α,11β,17β)-11-(4-Bromophenyl)-17-(cyclopropylhydroxymethyl)-5-hydroxyestr-9-en-3-one cyclic 1,2-ethanediyl acetal According to the procedures described in example 1 steps e and f (17β)-17-(cyclopropylhydroxymethyl)estra-5(10),9 (11)-dien-3-one cyclic 1,2-ethanediyl acetal was transformed into the title compound (26% yield). $^1$H NMR (400 MHz, CDCl$_3$): δ 0.12-0.57 (m, 7H), 0.79-0.89 (m, 1H), 1.10-2.12 (m, 17H), 2.27-2.40 (m, 2H), 2.65-2.76 (m, 2H), 3.88-4.03 (m, 4H), 4.14 (d, J=7 Hz, 1H), 4.34 (s, 1H), 7.08-7.13 (m, 2H), 7.32-7.36 (m, 2H).

d. (5α,11β,17β)-11-(4-Bromophenyl)-17-(cyclopropylcarbonyl)-5-hydroxyestr-9-en-3-one cyclic 1,2-ethanediyl acetal To a solution of (5α,11β,17β)-11-(4-bromophenyl)-17-(cyclopropylhydroxymethyl)-5-hydroxyestr-9-en-3-one cyclic (1,2-ethanediyl acetal) (726 mg, 1.3 mmol) in acetone (25 mL), 4-methylmorpholine N-oxide (438 mg, 3.7 mmol) and tetra-N-propylammonium perruthenate (VII) (28 mg, 0.08 mmol) were added and the reaction mixture was stirred for 2 hours at room temperature under a nitrogen atmosphere. Silica and heptane (14 mL) were added and the mixture was stirred for 1 hour, then filtered through dicalite and washed properly with ethyl acetate. The filtrate was evaporated to dryness to give (5α,11β,17β)-11-(4-bromophenyl)-17-(cyclopropylcarbonyl)-5-hydroxyestr-9-en-3-one cyclic 1,2-ethanediyl acetal (732 mg, 1.3 mmol, 100% yield). $^1$NMR (400 MHz, CDCl$_3$): δ 0.21 (s, 3H), 0.80-2.39 (m, 22H), 2.66-2.74 (m, 2H), 3.88-4.05 (m, 4H), 4.23 (d, J=7 Hz, 1H), 4.37 (s, 1H), 7.06-7.10 (m, 2H), 7.34-7.38 (m, 2H).

e. (11β,17β)-11-(4-Bromophenyl)-17-cyclopropylcarbonyl-4,9-dien-3-one

According to the procedure described in example 1 step g (5α,11β,17β)-11-(4-bromophenyl)-17-(cyclopropylcarbonyl)-5-hydroxyestr-9-en-3-one cyclic 1,2-ethanediyl acetal was transformed into the title compound (65% yield). $^1$NMR (400 MHz, CDCl$_3$): δ 0.27 (s, 3H), 0.83-2.83 (m, 22H), 4.34 (d, J=7 Hz, 1H), 5.79 (s, 1H), 7.02-7.07 (m, 2H), 7.37-7.42 (m, 2H).

f. (11β,17β)-17-Cyclopropylcarbonyl-11-[4-(3-pyridinyl)phenyl]estra-4,9-dien-3-one (11β,17β)-11-(4-Bromophenyl)-17-cyclopropylcarbonyl-4,9-dien-3-one was transformed into crude title compound using the procedure described in example 1 step h. Purification by preparative LCMS followed by lyophilisation gave the title compound (66% yield). $^1$NMR (400 MHz, CDCl$_3$): δ 0.32 (s, 3H), 0.84-2.82 (m, 21H), 2.92 (d, J=13 Hz, 1H), 4.46 (d, J=7 Hz, 1H), 5.80 (s, 1H), 7.27-7.32 (m, 2H), 7.34 (dd, J=8 and 5 Hz, 1H), 7.49-7.54 (m, 2H), 7.86 (dt, J=8 and 1 Hz, 1H), 8.58 (d, J=5 Hz, 1H), 8.84 (d, J=1 Hz, 1H).

Example 19

Preparation of (11β,17β)-17-cyclopropylcarbonyl-11-[4-(6-methoxypyridin-3-yl)phenyl]estra-4,9-dien-3-one (11β,17β)-11-(4-Bromophenyl)-17-cyclopropylcarbonyl-4,9-dien-3-one was transformed into crude title compound using the procedure described in example 1 step h using 6-methoxy-3-pyridinylboronic acid as reagent. Purification by preparative LCMS followed by lyophilisation gave the title compound. (60% yield). $^1$NMR (400 MHz, CDCl$_3$): δ 0.32 (s, 3H), 0.83-2.81 (m, 21H), 2.91 (d, J=13 Hz, 1H), 3.98 (s, 3H), 4.44 (d, J=7 Hz, 1H), 5.80 (s, 1H), 6.80 (d, J=8 Hz, 1H), 7.22-7.26 (m, 2H), 7.42-7.46 (m, 2H), 7.77 (dd, J=8 and 2 Hz, 1H), 8.37 (d, J=2 Hz, 1H).

Example 20

Preparation of (11β,17β)-17-cyclopropylcarbonyl-17-methyl-11-[4-(3-pyridinyl)-phenyl]estra-4,9-dien-3-one a. (17β)-17-(Cyclopropylcarbonyl)-17-methylestra-5(10),9(11)-dien-3-one cyclic 1,2-ethanediyl acetal L-selectride (3.0 mL, 3.0 mmol, 1M in THF) was slowly added to a cooled (−78° C.) and stirred solution of 17-(cyclopropylcarbonyl)estra-5(10),9(11),16-trien-3-one cyclic 1,2-ethanediyl acetal (500 mg, 1.4 mmol) and 1,3-dimethyl-3,4, 5,6-tetrahydro-2(1H)-pyrimidinone (0.33 mL, 2.7 mmol) in dry THF (20 mL) under a nitrogen atmosphere. After 1 hour at −78° C. methyl iodide (1.7 mL, 27 mmol) was added. The reaction mixture was stirred for an additional 1.5 hours while the temperature raised to −30° C. The reaction mixture was poured into water and extracted with ethyl acetate. The combined organic layers were washed with a saturated aqueous NaHCO$_3$ solution and brine, dried (MgSO$_4$) and the solvents were evaporated in vacuo. The crude product was purified by column chromatography (SiO$_2$, heptane/ethyl acetate=9/1, v/v) to give (17β)-17-(cyclopropylcarbonyl)-17-methylestra-5(10),9(11)-dien-3-one cyclic 1,2-ethanediyl acetal (255 mg 0.67 mmol, 49% yield). $^1$NMR (400 MHz, CDCl$_3$): δ 0.67 (s, 3H), 0.78-2.72 (m, 27H), 1.23 (s, 3H), 3.96-4.02 (m, 4H), 5.57-5.61 (m, 1H).

b. (11β,17β)-17-Cyclopropylcarbonyl-17-methyl-11-[4-(3-pyridinyl)phenyl]estra-4,9-dien-3-one (17β)-17-(Cyclopropylcarbonyl)-17-methylestra-5(10),9 (11)-dien-3-one cyclic 1,2-ethanediyl acetal was transformed into crude title compound using the procedures described in example 1 steps e, f, g and h. Purification by HPLC followed by lyophilisation gave the title compound. (19% yield over these 4 steps). $^1$NMR (400 MHz, CDCl$_3$): δ 0.42 (s, 3H), 0.80-2.82 (m, 24H), 2.28 (s, 3H), 4.48 (d, J=8 Hz, 1H), 5.80 (s, 1H), 7.30 (d, J=8 Hz, 1H), 7.34 (dd, J=4 and 8 Hz, 1H), 7.50 (d, J=8 Hz, 1H), 7.85 (dt, J=2 and 8 Hz, 1H), 8.57 (dd, J=2 and 4 Hz, 1H), 8.84 (d, J=2 Hz, 1H).

Example 21

Preparation of (11β,16α,17β)-17-cyclopropylcarbonyl-16,17-dihydro-11-[4-(3-pyridinyl)phenyl]-3'H-cyclopropa[16,17]estra 4,9,16-trien-3-one a (11β,16α,17β)-17-(Cyclopropylcarbonyl)-16,17-dihydro-3'H-cyclopropa[16,17]estra-5(10),9(11),16-trien-3-one cyclic 1,2-ethanediyl acetal Sodium hydride (60% oil dispersion, 197 mg, 4.9 mmol) was added to a stirred solution of trimethylsulfoxonium iodide (960 mg, 1.1 mmol) in DMSO (20 mL) under a nitrogen atmosphere, After 30 minutes a solution of 17-(cyclopropylcarbonyl)estra-5(10),9(11),16-trien-3-one cyclic (1,2-ethanediyl acetal) (400 mg, 1.1 mmol) in dry THF (4 mL) was added. After 1 hour the reaction mixture was poured into ice-water and extracted with ethyl acetate. The combined organic layers were washed with brine, dried ($MgSO_4$) and the solvents were evaporated in vacuo. The crude product was purified by column chromatography ($SiO_2$, gradient heptane/ethyl acetate=9/1, v/v to heptane/ethyl acetate=3/7, v/v) to give (16α,17β)-17-(cyclopropylcarbonyl)-16,17-dihydro-3'H-cyclopropa[16,17]estra-5(10),9(11),16-trien-3-one cyclic 1,2-ethanediyl acetal (102 mg 0.25 mmol, 91% yield). $^1$NMR (400 MHz, $CDCl_3$): δ 0.72-2.50 (m, 28H), 0,98 (s, 3H), 3.97-4.02 (m, 4H), 5.56-5.60 (m, 1H).

b. (11β,16α,17β)-17-cyclopropylcarbonyl-16,17-dihydro-11-[4-(3-pyridinyl)phenyl]-3'H-cyclopropa[16,17]estra-4,9,16-trien-3-one (16α,17β)-17-(cyclopropylcarbonyl)16,17-dihydro-3'H-cyclopropa[16,17]estra-5(10),9(11),16-trien-3-one cyclic 1,2-ethanediyl acetal was transformed into crude title compound using the procedures described in example 1 steps e, f, g and h. Purification by HPLC followed by lyophilisation gave the title compound. (24% yield over these 4 steps). $^1$NMR (400 MHz, $CDCl_3$): δ 0.70 (s, 3H), 0.68-2.78 (m, 23H), 3.03 (d, J=12, 1H), 4.41 (d, J=8 Hz, 1H), 5.78 (s, 1H), 7.31 (d, J=8 Hz, 1H), 7.35 (dd, J=4 and 8 Hz, 1H), 7.49 (d, J=8 Hz, 1H), 7.86 (dt, J=2 and 8 Hz, 1H), 8.57 (dd, J=2 and 5 Hz, 1H), 8.83 (d, J=3 Hz, 1H).

Example 22

Preparation of (11β,16α,17β)-17-cyclopropylcarbonyl-16-methyl-11-[4-(3-pyridinyl)-phenyl]estra-4,9-dien-3-one 3-oxime Hydroxylamine hydrochloride (20 mg, 0.30 mmol) and water (1 mL) were added to a stirred solution of 100 mg (0.20 mmol) of (11β,16α,17β)-17-cyclopropylcarbonyl-16-methyl-11-[4-(3-pyridinyl)phenyl]estra-4,9-dien-3-one in dioxane (2 mL). The reaction mixture was stirred overnight at room temperature and then extracted three times with dichloromethane. The combined organic layers were dried through a phase separate filter and evaporated to dryness. Purification of the crude product by HPLC followed by lyophilisation gave (11β,16α,17β)-17-cyclopropylcarbonyl-16-methyl-11-[4-(3-pyridinyl)phenyl]estra-4,9-dien-3-one 3-oxime as an E/Z mixture (2:1) (85 mg, 0.17 mmol, 84% yield). $^1$H NMR (400 MHz, $CDCl_3$): δ 0.31 and 0.32 (2×s, in total 3H), 0.83-2.95 (m, 25H), 4.37-4.42 (m, 1H), 5.89 and 6.55 (2×s, in total 1H), 7.26-7.32 (m, 2H), 7.35 (dd, J=8 and 5 Hz, 1H), 7.47-7.51 (m, 2H), 7.86 (dt, J=8 and 1 Hz, 1H), 8.57 (dd, J=5 and 1 Hz, 1H), 8.84 (d, J=1 Hz, 1H).

Example 23

Preparation of (11β)-11-[4-(3-pyridinyl)phenyl]-17,24-cyclo-19,21-dinorchola 4,9-diene-3,20-dione According to the procedures described in example 1 steps e, f, g and h 17,24-cyclo-19,21-dinorchola-5(10),9(11)-diene-3,20-dione cyclic 3-(1,2-ethanediyl acetal) (U.S. Pat. No. 5,084,450) was transformed into the crude title compound. Purification by preparative HPLC followed by lyophilisation gave the title compound (18% yield). $^1$H NMR (400 MHz, $CDCl_3$): δ 0.47 (s, 3H), 1.24-2.82 (m, 22H), 4.48 (d, J=7 Hz, 1H), 5.80 (s, 1H), 7.23-7.27 (m, 2H), 7.35 (dd, J=8 and 4 Hz, 1H), 7.46-7.51 (m, 2H), 7.84 (dt, J=8 and 1 Hz, 1H), 8.58 (dd, J=4 and 1 Hz, 1H), 8.82 (d, J=1 Hz, 1H).

Example 24

Preparation of (11β)-11-[4-(6-methoxypyridin-3-yl)phenyl]-17,24-cyclo-19,21-dinorchola 4,9-diene-3,20-dione Using the procedures applied in example 25 and using 6-methoxy-3-pyridinylboronic acid as borate in the last step the title compound was obtained from 17,24-cyclo-19,21-dinorchola-5(10),9(11)-diene-3,20-dione cyclic 3-(1,2-ethanediyl acetal) (17% yield). $^1$H NMR (400 MHz, $CDCl_3$): δ 0.47 (s, 3H), 1.25-2.81 (m, 22H), 3.98 (s, 3H), 4.46 (d, J=7 Hz, 1H), 5.80 (s, 1H), 6.80 (d, J=9 Hz, 1H), 7.18-7.22 (m, 2H), 7.40-7.44 (m, 2H), 7.75 (dd, J=9 and 2 Hz, 1H), 8.36 (d, J=2 Hz, 1H).

Example 25

Preparation of (11β)-11-[4-(3-pyridinyl)phenyl]-17,24-cyclo-19,21-dinorchola-4,9-diene-3,20-dione hydrochloride Using the procedure described in example 2 (11β)-11-[4-(3-pyridinyl)phenyl]-17,24-cyclo-19,21-dinorchola-4,9-diene-3,20-dione was transformed into (11β)-11-[4-(3-pyridinyl)phenyl]-17,24-cyclo-19,21-dinorchola-4,9-diene-3,20-dione hydrochloride (100% yield). $^1$H NMR (600 MHz, $CDCl_3$): δ 0.45 (s, 3H), 1.33-2.80 (m, 22H), 4.50 (d, J=7 Hz, 1H), 5.82 (s, 1H), 7.30-7.33 (m, 2H), 7.50-7.53 (m, 2H), 7.69-7.72 (m, 1H), 8.25 (d, J=7 Hz, 1H), 8.64 (d, J=5 Hz, 1H), 8.90 (d, J=1 Hz, 1H).

Example 26

(6β,11β,16α,17β)-17-cyclopropylcarbonyl-6,16-dimethyl-11-[4-(3-pyridinyl)-phenyl]estra-4,9-dien-3-one According to the procedures described in example 1 (6β)-6-methylestra-5(10),9(11)-diene-3,17-dione cyclic 3-(1,2-ethanediyl acetal) was transformed into the crude title compound. Purification by preparative HPLC followed by lyophilisation gave the title compound (14% yield). $^1$NMR (400 MHz, $CDCl_3$): δ 0.38 (s, 3H), 0.85-2.88 (m, 24H), 0.99 (d, J=8 Hz, 3H), 1.32 (d, J=8 Hz, 3H), 4.46 (d, J=8 Hz, 1H), 5.84 (s, 1H), 7.27 (d, J=8 Hz, 1H), 7.41 (dd, J=5 and 8 Hz, 1H), 7.53 (d, J=8 Hz, 1H), 7.94 (dt, J=2 and 8 Hz, 1H), 8.59 (dd, J=2 and 4 Hz, 1H), 8.90 (d, J=2 Hz, 1H).

Example 27

Preparation of (11β,16α,17β)-17-cyclopropylcarbonyl-16-methyl-11-[4-(pyrimidin-2-yl)phenyl]estra-4,9-dien-3-one According to the procedure described in example 8, (11β,16α,17β)-11-(4-bromophenyl)-17-cyclopropylcarbonyl-16-methylestra-4,9-dien-3-one and 2-tributylstannylpyrimidine were heated for four hours at 110° C. to give the title compound (17% yield). $^1$H NMR (400 MHz, $CDCl_3$): δ 0.32 (s, 3H), 0.83-2.87 (m, 24H), 4.47 (d, J=7.0 Hz, 1H), 5.80 (s, 1H), 7.18 (t, J=4.7 Hz, 1H), 7.28-7.31 (m, 2H), 8.32-8.35 (m, 2H), 8.79 (d, J=4.7 Hz, 2H).

Example 28

Progesterone Receptor-B Activity in a Transactivation

The progestagenic activity of a compound of the invention ($EC_{50}$ and intrinsic agonistic activity) was determined in an in vitro bioassay of Chinese hamster ovary (CHO) cells as described by W. G. E. J. Schoonen et al. (Anal. Biochem. 261 (1998), 222-224). The antiprogestagenic activity of a compound of the invention ($IC_{50}$ and intrinsic antagonistic activity) was determined in a setting comparable to the agonistic assay described above, by the inhibition of the transactivation via the progesterone receptor-B of the enzyme luciferase in the presence of 0.1 nM of the inducer (16α)-16-ethyl-21-hydroxy-19-norpregn-4-ene-3,20-dione. The efficacy of the antagonistic effect was expressed as the percentage of the effect produced by a standard antagonist, (6β,11β,17β)-11-[4-(dimethylamino)phenyl]-4',5'-dihydro-6-methylspiro[estra-4,9-diene-17,2'(3'H)-furan]-3-one. Agonistic ligands do not inhibit transactivation of luciferase activity produced by the inducer, whereas strong and weak antiprogestagens as well as compounds with a mixed progestagenic/antiprogestagenic profile can inhibit transactivation dependent on the dose level used of the antiprogestagen or mixed-profile compound in question.

It will be recognized by those skilled in the art that, in the setting described above, the EC50 determined is more or less absolute and depends on the intrinsic property of the tested compound itself, however, the IC50 depends on the amount and agonistic EC50 of the inducer as well as on the intrinsic property of the tested compound itself. Thus, with the same amount of inducer, a relatively strong antagonist will be able to produce a measurable IC50 whereas a relatively weak antagonist may fail to produce a detectable result.

TABLE

| Example | PRBagoEC50 [M] | PRBago Eff (%) | PRBant EC50 [M] | PRBant Eff (%) |
|---|---|---|---|---|
| 1 | 2E-10 | 49.2 | 2.67E-10 | 46.4 |
| 2 | 3.4E-10 | 44.5 | 3.3E-09 | 47 |
| 3 | 1.2E-10 | 41.5 | 6.28E-10 | 59 |
| 4 | 1.1E-09 | 46.5 | 4.7E-10 | 43 |
| 5 | 4.9E-10 | 50.5 | 8.48E-09 | 50 |
| 6 | 1.3E-09 | 54 | 2.8E-08 | 34 |
| 7 | 1E-09 | 50 | 3.14E-09 | 24 |
| 8 | 3.6E-10 | 50.5 | 3.64E-09 | 37 |
| 9 | 1.13E-09 | 54 | 1.3E-09 | 35 |
| 10 | 2.6E-09 | 49.25 | 1.48E-08 | 32.5 |
| 11 | 1.7E-09 | 56 | 8E-10 | 35 |
| 12 | 4E-09 | 56 | 2.5E-09 | 26.5 |
| 13 | 6.6E-10 | 46.8 | 6.10E-10 | 38 |
| 14 | 5.7E-09 | 49.75 | 2.9E-08 | 34.5 |
| 15 | 7.4E-10 | 41.4 | 9.80E-10 | 44.5 |
| 16 | 2.3E-10 | 34 | 5.96E-10 | 53 |
| 17 | 1.3E-09 | 42 | 7.89E-09 | 51.7 |
| 18 | 8.2E-10 | 36 | 7.51E-10 | 66 |
| 19 | 5.1E-10 | 28.3 | 4.27E-10 | 57 |
| 20 | 4.9E-10 | 37.5 | 1.3E-10 | 58 |
| 21 | 2E-09 | 18 | 1.4E-09 | 58 |
| 22 | 6.4E-10 | 43 | 1.47E-09 | 32 |
| 23 | 2.9E-10 | 17 | 3.25E-10 | 70.8 |
| 24 | 1.5E-10 | 20 | 5.46E-10 | 62 |
| 25 | 4.8E-10 | 17 | 1.1E-09 | 66 |
| 26 | 8.09E-10 | 46 | 2.75E-09 | 17 |
| 27 | 2.54E-09 | 52 | 3.25E-09 | >27 |

The invention claimed is:

1. A compound according to Formula I, wherein

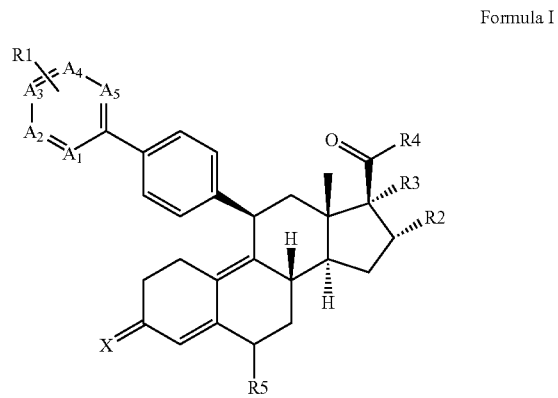

Formula I

X is O, NOH, NO(1-4C)alkyl, NO(1-4C)acyl;

A1-A5 are C, substituted with R1, or N, provided that at least one and not more than three of A1-A5 are N; or one or two of A1, A2 and A5 are N, and the others are C, substituted with R1, and A3 and A4 together represent a fused benzo ring or a fused five- or six-membered nitrogen-containing aromatic ring, both optionally substituted with one or more halogen and/or (1-4C)alkyl;

each R1 is independently selected from H, halogen, (1-4C) alkyl and (1-4C)alkoxy;

R2 is H, (1-4C)alkyl, or (1-6C) alkenyl, both optionally substituted with an (6-10C)aryl group, which is optionally substituted with one or more halogen and/or (1-4C) alkyl; and R3 is H or (1-4C)alkyl, optionally substituted with one or more halogen; and R4 is cyclopropyl or cyclopropenyl both optionally substituted with one or more halogen and/or (1-4C)alkyl; or R2 together with R3 forms a 3-, 4-, 5- or 6-membered carbocyclic ring; and R4 is cyclopropyl or cyclopropenyl both optionally substituted with one or more halogen and/or (1-4C)alkyl); or R2 is H or (1-4C)alkyl; and R3 together with R4 forms a 5-, 6- or 7-membered saturated or unsaturated carbocyclic ring;

R5 is H or (1-4C)alkyl;

or a pharmaceutically acceptable salt thereof.

2. A compound according to claim 1, wherein A1-A5 are C, substituted with R1, or N, provided that at least one and not more than three of A1-A5 are N.

3. A compound according to claim 1, wherein one or two of A1, A2 and A5 are N, and the others are C, substituted with R1, and A3 and A4 together represent a fused benzo ring or a fused five- or six-membered nitrogen-containing aromatic ring, both optionally substituted with halogen and/or (1-4C) alkyl.

4. A compound according to claim 1, wherein

R2 is H, (1-4C)alkyl or (1-6C)alkenyl, both optionally substituted with an (6-10C)aryl group, which is optionally substituted with one or more halogen and/or (1-4C) alkyl; and R3 is H or (1-4C)alkyl, optionally substituted with one or more halogen; and R4 is cyclopropyl or cyclopropenyl, both optionally substituted with one or more halogen and/or (1-4C)alkyl.

5. A compound according to claim 1,
wherein
R2 together with R3 forms a 3-, 4-, 5- or 6-membered carbocyclic ring; and
R4 is cyclopropyl or cyclopropenyl, both optionally substituted with one or more halogen and/or (1-4C)alkyl.

6. A compound according to claim 1, wherein
R2 is H or (1-4C)alkyl; and
R3 together with R4 forms a 5-, 6- or 7-membered saturated or unsaturated carbocyclic ring.

7. A compound according to claim 2, wherein
R2 is H, (1-4C)alkyl or (1-6C)alkenyl, both optionally substituted with an (6-10C)aryl group, which is optionally substituted with one or more halogen and/or (1-4C)alkyl; and
R3 is H or (1-4C)alkyl optionally substituted with one or more halogen; and
R4 is cyclopropyl or cyclopropenyl both optionally substituted with one or more halogen and/or (1-4C)alkyl.

8. A compound according to claim 2,
wherein
R2 together with R3 forms a 3-, 4-, 5- or 6-membered carbocyclic ring; and
R4 is cyclopropyl or cyclopropenyl, both optionally substituted with one or more halogen and/or (1-4C)alkyl.

9. A compound according to claim 2, wherein
R2 is H or (1-4C)alkyl; and
R3 together with R4 forms a 5-, 6- or 7-membered saturated or unsaturated carbocyclic ring.

10. A compound according to claim 3, wherein
R2 is H, (1-4C)alkyl or (1-6C)alkenyl, both optionally substituted with an (6-10C)aryl group which is optionally substituted with one or more halogen and/or (1-4C)alkyl; and
R3 is H or (1-4C)alkyl optionally substituted with one or more halogen; and
R4 is cyclopropyl or cyclopropenyl both optionally substituted with one or more halogen and/or (1-4C)alkyl.

11. A compound according to claim 3, wherein
R2 together with R3 forms a 3-, 4-, 5- or 6-membered carbocyclic ring; and
R4 is cyclopropyl or cyclopropenyl, both optionally substituted with one or more halogen and/or (1-4C)alkyl.

12. A compound according to claim 3,
wherein
R2 is H or (1-4C)alkyl; and
R3 together with R4 forms a 5-, 6- or 7-membered saturated or unsaturated carbocyclic ring.

13. A compound according to claim 1, wherein X is O.

14. A compound according to claim 4, wherein R4 is cyclopropyl.

15. A compound according to claim 5, wherein R4 is cyclopropyl.

16. A compound according to claim 2, wherein A1, A3, A4 and A5 are C, substituted with R1, and A2 is N.

17. A compound according to claim 13, wherein
A1, A3, A4 and A5 are C, substituted with R1, and A2 is N;
R2 is H, (1-4C)alkyl or (1-4C)alkenyl; and
R3 is H or (1-4C)alkyl, optionally substituted with one or more halogen; and
R4 is cyclopropyl; or
R2 together with R3 forms a 3-, 4-, 5- or 6-membered carbocyclic ring; and
R4 is cyclopropyl.

18. A compound according to claim 13, wherein
A1, A3, A4 and A5 are C;
A2 is N;
R1 is H
R2 is ethenyl;
R3 is H;
R4 is cyclopropyl; and
R5 is H.

19. A compound according to claim 4, wherein R2 is H, (1-4C)alkyl or (1-4C)alkenyl.

20. A pharmaceutical composition comprising a compound according to claim 1 or a pharmaceutically acceptable salt thereof, and a pharmaceutically acceptable carrier.

21. A method of contraception comprising administering a pharmaceutically effective amount of a compound according to claim 1 or a pharmaceutically acceptable salt thereof to a subject in need thereof.

22. A method of treating a gynaecological disorder selected from the group consisting of endometriosis, dysmenorrhea, dysfunctional uterine bleeding and severe premenstrual syndrome, the method comprising administering a pharmaceutically effective amount of a compound according to claim 1 or a pharmaceutically acceptable salt thereof to a subject in need thereof.

23. A method of hormone replacement therapy comprising administering a pharmaceutically effective amount of a compound according to claim 1 or a pharmaceutically acceptable salt thereof to a subject in need thereof.

24. A compound of the formula

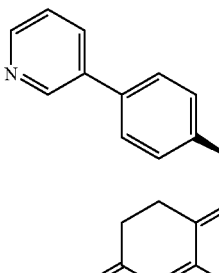

25. A pharmaceutical composition comprising a compound according to claim 24 or a pharmaceutically acceptable salt thereof, and a pharmaceutically acceptable carrier.

26. The method according to claim 22, wherein the gynaecological disorder is endometriosis.

27. A method of treating a gynaecological disorder selected from the group consisting of endometriosis, dysmenorrhea, dysfunctional uterine bleeding and severe premenstrual syndrome, the method comprising administering the compound according to claim 24 or a pharmaceutically acceptable salt thereof to a subject in need thereof.

28. The method according to claim 27, wherein the gynaecological disorder is endometriosis.

* * * * *